United States Patent
Ishii et al.

(10) Patent No.: US 7,863,235 B2
(45) Date of Patent: Jan. 4, 2011

(54) METHOD OF ACTIVATING α-AMYLASE WITH OXIDIZING AGENTS

(75) Inventors: Yoko Ishii, Wakayama (JP); Masafumi Nomura, Wakayama (JP); Shitsuu Shikata, Wakayama (JP)

(73) Assignee: Kao Corporation, Tokyo (JP)

( * ) Notice: Subject to any disclaimer, the term of this patent is extended or adjusted under 35 U.S.C. 154(b) by 592 days.

(21) Appl. No.: 11/296,423

(22) Filed: Dec. 8, 2005

(65) Prior Publication Data

US 2006/0154845 A1   Jul. 13, 2006

(30) Foreign Application Priority Data

Dec. 9, 2004  (JP)  ............................. 2004-356199
Oct. 27, 2005  (JP)  ............................. 2005-313122

(51) Int. Cl.
*C11D 3/38* (2006.01)
*C11D 3/00* (2006.01)
*C12N 9/26* (2006.01)

(52) U.S. Cl. ...................... 510/306; 510/392; 510/374; 510/302

(58) Field of Classification Search ........................ None
See application file for complete search history.

(56) References Cited

U.S. PATENT DOCUMENTS

2003/0078179 A1* 4/2003 Ghosh et al. ................ 510/392

2003/0119698 A1* 6/2003 Busch et al. ................ 510/302
2003/0191040 A1* 10/2003 Adriaanse et al. ........... 510/267

FOREIGN PATENT DOCUMENTS

| JP | 5-507615 A | 11/1993 |
| JP | 8-256768 A | 10/1996 |
| JP | 2000-37186 A | 2/2000 |
| JP | 2000-245453 A | 9/2000 |
| WO | WO-91/19794 A1 | 12/1991 |
| WO | WO-91/19807 A1 | 12/1991 |
| WO | WO9402597 * | 2/1994 |
| WO | WO-96/30481 A1 | 10/1996 |

OTHER PUBLICATIONS

R.C. Srivastava et al., "Activation of Enzymes by Reversed Micelles", Biotechnology and Bioengineering, vol. XXIX, p. 901-902, 1987.
Kishio Matsuura et al., "Proteochemical, Immunological and Enzymatic Properties of Two Amylase Components from Human Pancreatic Juice", Clin Biochem., 16 (4):224-228, 1983.

* cited by examiner

*Primary Examiner*—Lisa J Hobbs
(74) *Attorney, Agent, or Firm*—Birch, Stewart, Kolasch & Birch, LLP

(57) ABSTRACT

The invention provides an activation method of α-amylase. α-Amylase or particles containing the same are contacted with an oxidizing agent or particles containing the same. After contacting, the activated α-amylase can be separated from the oxidizing agent. After contacting, α-amylase and the oxidizing agent can be incorporated in the form of a mixture into a detergent base to give a detergent composition.

20 Claims, No Drawings

METHOD OF ACTIVATING α-AMYLASE WITH OXIDIZING AGENTS

FIELD OF THE INVENTION

The present invention relates to a method of activating α-amylase and to α-amylase activated by the method.

BACKGROUND OF THE INVENTION

α-Amylase (1,4-α-D-glucan glucanohydrolase [EC3.2.1.1]) is an endo-type enzyme which randomly cleaves α-1,4 glucoside linkages of starch, glycogen etc. This enzyme is widely used industrially in starch processing, food processing, fiber processing, fermentation, pharmaceutical preparations, clinical examination and detergents, and is derived from a wide variety of sources such as microorganisms, plants and animals.

Conventionally, this industrially very important enzyme is not always satisfactory in respect of its activity and cost, and as a means for solving this problem, an increase in productivity of the enzyme and reinforcement of the catalytic ability of the enzyme have been attempted by genetic recombination and protein engineering technology, and a method of improving the reaction rate of the enzyme in an enzyme reaction system, that is, a method of activating the enzyme reaction, has been examined.

With respect to the method of activating the enzyme, there are reports on activation by adding a specific polymer to an enzyme reaction system (JP-A(W) 5-507615), activation by adding chlorine ions to specific amylase (Clin. Biochem., 16, 224-228 (1983)), the enhancement of the enzyme activity by utilizing a reverse phase micelle system obtained by adding Tween 20 (polyoxyethylene sorbitan monolaurate) to n-hexane (Biotechnol. Bioeng., 29, 901-902 (1987)), and the enhancement of the enzyme activity by adding an alkyl sulfate and/or alkyl sulfonate having an alkyl group of specific length to an enzyme reaction system (JP-A 8-256768). Further, a method of activating the enzyme in a step prior to the enzyme reaction by previously dissolving the enzyme in electrolytic water (JP-A 2000-245453) and a method of activating the enzyme by dissolving the enzyme in an exothermic inorganic salt (JP-A 2000-37186) have been reported.

With respect to the method of producing a detergent composition containing the enzyme, many literatures have reported separate after-blending of the enzyme, a bleaching agent etc. into a detergent base obtained by various granulation procedures.

DISCLOSURE OF THE INVENTION

The invention provides a method of activating α-amylase, which includes a step of contacting A) α-amylase or particles containing α-amylase with B) an oxidizing agent or particles containing an oxidizing agent.

The invention then provides a method of activating α-amylase, which includes steps of contacting A) α-amylase or particles containing α-amylase with B) an oxidizing agent or particles containing an oxidizing agent and separating A) α-amylase or particles containing α-amylase after the contacting step.

The invention then provides a method of producing activated α-amylase, which includes steps of contacting A) α-amylase or particles containing α-amylase with B) an oxidizing agent or particles containing an oxidizing agent and separating A) α-amylase or particles containing α-amylase after the contacting step.

The invention then provides α-Amylase which is obtainable by the above shown method and a detergent composition containing the α-amylase.

Moreover the invention provides a method of producing an α-amylase-containing detergent composition, which including a detergent base with a mixed and treated material obtained by mixing A) α-amylase or particles containing α-amylase with B) an oxidizing agent or particles containing an oxidizing agent.

DETAILED EXPLANATION OF THE INVENTION

These activation methods can increase the rate of enzyme reaction to a certain degree, but cannot be said to be satisfactory in respect of the activation power. These activation methods have a problem that large-scale facilities are required for activation treatment of the enzyme in the form of a solution, and because separation of the activator for enzyme reaction is difficult, the final product is contaminated therewith to decrease its product value, and therefore these methods are problematic for use as general-purpose techniques.

Under these circumstances, the present inventors made extensive study on the method of activating α-amylase, and as a result, they found that α-amylase can be significantly activated by contacting the α-amylase and an oxidizing agent with each other in solid forms, respectively, for pretreatment for enzyme reaction, and the present invention was thereby completed.

The present invention provides an activation method of significantly increasing the enzyme activity of α-amylase by easy operation. The present invention further provides a detergent composition containing α-amylase obtained by the activation method.

Hereinafter, the terms "α-amylase" and "oxidizing agent" may encompass α-amylase-containing particles and oxidizing agent-containing particles, respectively.

According to the present invention, activated α-amylase can be obtained by an easy method. The oxidizing agent used in the contacting step can be easily separated from the α-amylase, and the activated α-amylase with fewer impurities can be widely used as a component in various industrial processes and detergents. The α-amylase activated according to the present invention can greatly contribute to reduction in the amount of the enzyme used and to reduction in the reaction time. The oxidizing agent used in activation in the present invention can be repeatedly used. Accordingly, the present invention also brings about an advantageous effect in an economical aspect in the enzyme reaction using α-amylase and its applied technology.

According to the present invention, α-amylase and the oxidizing agent can be incorporated, in a mixed state without separation, into a composition such as a detergent. This operation is particularly effective when the composition contains the oxidizing agent as an active ingredient. That is, the composition can be endowed with a higher enzyme effect than by a conventional method of adding α-amylase and an oxidizing agent separately, while there is an advantage in process that introduction of α-amylase and the oxidizing agent can be simultaneously completed.

With regard to the α-amylase as the subject of the present invention, it is possible to employ α-amylase obtained from many living creatures, for example microorganisms such as *Bacillus subtilis Marburg, Bacillus subtilis natto, Bacillus amyloliquefaciens, Bacillus licheniformis, Bacillus cereus, Bacillus macerans, Pseudomonas stutzeri, Klebusiella aerogenes*, etc., actinomyces such as *Steptomyces griseus* etc., fungi such as *Aspergillus oryzae*, *Aspergillus niger* etc., seeds of Gramineae and Leguminosae plants, and digestive glands of animals such as human and swine.

The α-amylase used in the present invention can be obtained by inoculating the above microorganism, a variant thereof, or a host cell etc. transformed with a recombinant vector having a DNA sequence encoding the enzyme or its variant onto a medium containing essential nutrients such as assimilable carbon and nitrogen sources etc., culturing it in a usual manner, and separating the formed enzyme by usual enzyme collection and purification methods. The enzyme solution obtained in this manner can be used as such, or may be used after further purification, crystallization, powdering or granulation by known methods (for example, JP-B 58-26315, JP-A (W) 7-500013, JP-A 62-255990, JP-A 9-48996).

The form of α-amylase used in the present invention includes (1) a dried product of the enzyme protein, (2) solids containing the enzyme protein, and (3) a liquid containing the enzyme protein, among which (1) and (2) are preferably used for the reason that after α-amylase is contacted with an oxidizing agent or particles containing the same, these can be easily separated from each other. When (1) or (2) is used, the average particle diameter thereof is preferably 20 to 4000 μm, more preferably 250 to 1000 μm.

The average particle diameter can be determined by attaching a standard sieve according to JIS K 8801, having sieve opening of 2000 to 37 μm and a receiving plate to a Ro-tap machine, manufactured by Heiko Seisakusho, with the tapping number: 156/min. and rolling number: 290/min., vibrating 100 g of a sample therein for 10 minutes to sieve it and calculating a median diameter from the obtained weight fractions with sieve sizes, respectively. When the median diameter obtained with the JIS K 8801 standard sieve is 50 μm or less, calculation may be made from an average value of Feret's diameter with a scanning electron microscope.

The concentration of α-amylase, in terms of a percent by weight of enzyme protein, is preferably 0.1 to 20%. The enzyme protein was quantified according to the Lowry method (Lowry, O. H. et al., J. Biol. Chem., 193, 265 (1951)) and expressed by using bovine serum albumin (BSA) (product number: A-7030, manufactured by SIGMA) as standard.

The oxidizing agent used in the present invention is not particularly limited insofar as it is solid, and can be used in any forms such as powder, granules, and granulated particles. The oxidizing agent includes at least one member selected from percarbonate, perborate, persulfate, permanganate, and perchlorate.

Specifically, sodium percarbonate, sodium perborate, a sodium tartrate/hydrogen peroxide adduct, a urea/hydrogen peroxide adduct, a sodium tripolyphosphate/hydrogen peroxide adduct, a sodium pyrophosphate/hydrogen peroxide adduct, a $4Na_2SO_4 \cdot 2H_2O_2/NaCl$ double salt, sodium peroxide, calcium peroxide, sodium persulfate, potassium persulfate, ammonium persulfate, their mixture forming sulfate ion radicals, potassium permanganate, sodium perchlorate, sodium hypochlorite etc.

In consideration of safety and easy handling for use, preferable among those described above are sodium percarbonate, sodium perborate, and sodium perchlorate. These oxidizing agents can be used alone or as a mixture of two or more thereof. The percarbonate which can be used is commercially available from Wako Pure Chemical Industries, Ltd., Mitsubishi Gas Chemical Company, Inc., Nippon Peroxide Co., Ltd., and Asahi Denka Kogyo K.K.; the perborate which can be used is available from Wako Pure Chemical Industries, Ltd., Mitsubishi Gas Chemical Company, Inc., Degussa-Huels Co., and Shaoxing Sino-USA (Meihua) Home Solution Co., Ltd.; and the perchlorate which can be used is available from Wako Pure Chemical Industries, Ltd., Mitsubishi Gas Chemical Company, Inc., etc. The oxidizing agent is preferably in the form of particles having an average particle diameter of 40 to 4000 μm, particularly 100 to 1500 μm.

Preferably, 1 IU (international unit) to 5 hundred million IU, especially 100 IU to 50 million IU, of α-amylase is contacted with the oxidizing agent in an amount corresponding to 1 g effective oxygen.

The activity of α-amylase is measured by a phadebas method illustrated in the Examples below.

The amount of effective oxygen in the oxidizing agent can be determined by the following iodometric method.

(Method of Measuring the Amount of Effective Oxygen)

The oxidizing agent is dissolved in 0.5% aqueous sulfuric acid, 10 ml of the resulting solution is sampled in a glass bottle with a cap (manufactured by Maruemu Co., Ltd.), 10 ml of 20 wt % aqueous sulfuric acid is added, then 10 ml of 10 wt % potassium iodide is added, and the sample is sealed and left at 40° C. for a predetermined time in the dark. Then, this sample is left, cooled to room temperature (25° C.) and titrated with a sodium thiosulfate standard. The amount of effective oxygen per g of the sample, defined by the equation (1) shown below, is measured. The period of time for which the sample is left until titration with the sodium thiosulfate standard is in such a range that the change in the amount of effective oxygen is within ±10%.

$$\text{Amount of effective oxygen per g of the sample} = [(N \times T/1000) \times F \times \frac{1}{2} \times 16]/X \quad (1)$$

X: Amount (g) of the oxidizing agent sample;
N: Normal of sodium thiosulfate;
T: Titration amount (ml) of sodium thiosulfate; and
F: Factor of sodium thiosulfate.

The time for which α-amylase is contacted with the oxidizing agent is preferably 10 seconds or more, more preferably 5 minutes to 2 months.

The temperature at which α-amylase is contacted with the oxidizing agent is preferably 5 to 80° C., more preferably 20 to 50° C. This temperature is the ambient temperature of the two components.

The absolute humidity under which α-amylase is contacted with the oxidizing agent is preferably 0.5 to 1000 $g/m^3$, more preferably 1.5 to 200 $g/m^3$. This humidity is the ambient humidity of the two components.

After α-amylase or particles containing the same are contacted with the oxidizing agent or particles containing the same, known methods can be used to separate them from each other. Such methods include, for example, a method of separating them depending on a difference in outward appearance, a method of separating them depending on a difference in particle diameter or absolute specific gravity. The latter method includes screening and air classification, and this screening includes vibrating screening, and the air classification includes dynamic, inertial, or centrifugal classification. The method of separation by a vibrating screen is preferable for easiness in operation. A vibrating sieve (model 502), sold by Dalton Co., Ltd. and Gyroshifter (model GS-132-25·AM) manufactured by Tokuju Kousakusho Co., Ltd. may be specifically used.

Particularly, the particle diameter distribution of α-amylase or particles containing the same is preferably different from that of the oxidizing agent or particles containing the same to such an extent that α-amylase can be sufficiently separated or recovered by screening or the like, and usually separation and recovery can be achieved when the two are sufficiently different from each other in average particle diameter. The difference between the minimum particle diameter of one particle group and the maximum particle diameter of the other particle group is for example preferably 1 μm or more.

The contacting is achieved by mixing α-amylase or particles containing the same with the oxidizing agent or particles containing the same, and when particles such as granulated particles are used, those having the above-mentioned particle diameter can be used to exhibit the same effect as achieved by directly mixing the two, regardless of the distribution (concentration distribution) of α-amylase or the oxidizing agent in the particles.

A detergent composition containing the α-amylase obtained according to the activation method described above has higher detergency than that of a composition containing untreated α-amylase.

In the present invention, a detergent composition can be produced by mixing and contacting A) α-amylase or particles containing the same with B) an oxidizing agent or particles containing the same, and then incorporating them in a mixed state without separation into a detergent base. The method of mixing and treating the component A) with the component B) includes a method of using a mixer used in production of a detergent composition, for example a container-rotating mixer such as a cylindrical mixer and V blender or a container-fixed mixer such as a ribbon mixer. As the detergent base, known detergent bases obtained by a typical process for producing a detergent composition, such as a spray-drying method, a dry neutralization method, a dry granulation method, an agitating granulation method, a milling granulation method or a wet granulation method can be used.

EXAMPLES

The following examples further describe and demonstrate embodiments of the present invention. The examples are given solely for the purpose of illustration and are not to be construed as limitations of the present invention.

Hereinafter, the method (phadebas method) used to measure the activity of α-amylase in the Examples is described.

<Method for Measuring the Activity of α-Amylase>

(1) Measurement of the Absorbance of a Sample

One tablet from Neo, Amylase Test "Daiichi" (product number: 701501-005, available from Daiichi Pure Chemicals Co., Ltd.) was added to 5 mL buffer (Britton-Robinson's Buffer, pH 8.5, 50 mM (Koichi Anan et al., Fundamental Biochemical Experimental Method 6 [in Japanese], p. 277, Maruzen Co., Ltd.)) and stirred for about 10 seconds, then 1 mL enzyme solution diluted with 2 mM aqueous calcium chloride was added, and the mixture was reacted at 50° C. for 15 minutes. 1 mL of 0.5 N aqueous sodium hydroxide was added to the solution under stirring to terminate the reaction, and then the reaction solution was centrifuged (400×g, 5 minutes) to precipitate insoluble components, and the supernatant thus obtained by centrifugation was measured for absorbance at 620 nm.

(2) Measurement of the Absorbance of a Blank

One tablet from Neo, Amylase Test "Daiichi" was added to 5 mL buffer (Britton-Robinson's Buffer, pH 8.5, 50 mM (Koichi Anan et al., Fundamental Biochemical Experimental Method 6 [in Japanese], p. 277, Maruzen Co., Ltd.)) and stirred for about 10 seconds. 1 mL of 0.5 N aqueous sodium hydroxide was added and stirred, then 1 mL enzyme solution was added, and the mixture was incubated at 50° C. for 15 minutes and centrifuged (400×g, 5 minutes). The supernatant thus obtained by centrifugation was measured for absorbance at 620 nm.

(3) Calculation of Enzyme Activity

The activity of amylase was calculated from the difference in absorbance between (1) and (2) in a calibration curve as a standard of an International Unit sample enclosed with Neo, Amylase Test "Daiichi".

Example 1

(1) α-Amylase and Oxidizing Agent

Duramyl 60T (α-amylase) commercially available from Novozymes A/S was sieved to give Duramyl 60T with a large particle diameter [(a1), average particle diameter (median diameter): 709 μm] from a fraction remaining on JIS standard 500 μm sieve. A percarbonate-based oxidizing agent SPC-D available from Mitsubishi Gas Chemical Company, Inc. was milled in a mortar to give oxidizing agent powder with a small particle diameter [(b1), average particle diameter (median diameter): 281 μm] from a fraction passing through JIS standard 500 μm sieve. 1 g of this oxidizing agent SPC-D (b1) expressed in terms of the amount of effective oxygen, was 0.12 g, and the enzyme activity of Duramyl 60T before the contacting step was 12000 IU/g. The median diameter is the diameter of particles corresponding to 50% in a distribution curve on the sieve.

(2) Mixing Ratio 3.0 g of Duramyl 60T (a1) and the oxidizing agent powder (b1) prepared in (1) above were mixed in weight ratios (enzyme/oxidizing agent) of 100/1, 10/1 and 1/10 in glass bottles (No. 3, manufactured by Maruemu Corporation) respectively, then capped, and contacted with each other at 25° C. and absolute humidity: 8 g/m$^3$ for 30 minutes. These mixtures were separated by JIS standard 500 μm sieve to recover Duramyl 60T (a1) after the contacting step. When the enzyme activity of the separated Duramyl 60T was measured by the method described above, the present products had a higher enzyme activity than that of the enzyme (control) not contacted with the oxidizing agent (Table 1).

TABLE 1

| ratio by weight (enzyme/oxidizing agent) | Relative activity (%)* |
|---|---|
| 100/1 | 133 |
| 10/1 | 150 |
| 1/10 | 201 |

*Relative activity: Enzyme activity relative to the enzyme activity [= 100%] of the enzyme (control) not contacted with the oxidizing agent.

(3) Contact Time 3.0 g of Duramyl 60T (a1) and 0.3 g of the oxidizing agent powder (b1) prepared in (1) above were mixed in a weight ratio (enzyme/oxidizing agent) of 10/1 in glass bottles (No. 3, manufactured by Maruemu Corporation), then capped, and contacted with each other at 25° C. and absolute humidity: 8 g/m$^3$ for 30 seconds, 5 minutes, 30 minutes, 3 days and 50 days respectively (indicated as "closed" in Table 2). These mixtures were separated by JIS standard 500 μm sieve. When the enzyme activity of the separated Duramyl 60T was measured by the method described above, the present products had a higher enzyme activity than that of the enzyme (control) not contacted with the oxidizing agent (Table 2).

(4) Temperature 3.0 g of Duramyl 60T (a1) and 0.3 g of the oxidizing agent powder (b1) prepared in (1) above were mixed in a weight ratio (enzyme/oxidizing agent) of 10/1 in glass bottles (No. 3, manufactured by Maruemu Corporation), then capped, and contacted with each other at 50° C. and absolute humidity: 8 g/m$^3$ for 30 minutes (indicated as "closed" in Table 2). These mixtures were separated by JIS standard 500 μm sieve. When the enzyme activity of the separated Duramyl 60T was measured by the method described above, the present products had a higher enzyme activity than that of the enzyme (control) not contacted with the oxidizing agent (Table 2).

(5) Humidity 3.0 g of Duramyl 60T (a1) and 0.3 g of the oxidizing agent powder (b1) prepared in (1) above were mixed in a weight ratio (enzyme/oxidizing agent) of 10/1 in glass bottles (No. 3, manufactured by Maruemu Corporation) and contacted with each other at 20° C. and absolute humidity: 11.2 g/m$^3$ for 60 minutes without capping. These mixtures were separated by JIS standard 500 μm sieve. When the enzyme activity of the separated Duramyl 60T was measured by the method described above, the present products had a higher enzyme activity than that of the enzyme (control) not contacted with the oxidizing agent (Table 2).

TABLE 2

| Contact temperature | Contact absolute humidity | Contact time | Relative activity (%) |
|---|---|---|---|
| 25° C. | 8 g/m$^3$ | 30 seconds | 136 |
| | | 5 minutes | 130 |
| | | 30 minutes | 150 |
| | | 3 days | 170 |
| | | 50 days | 153 |
| 50° C. | 8 g/m$^3$ | 30 minutes | 159 |
| 20° C. | 11.2 g/m$^3$ | 60 minutes | 120 |

*Contact ratio:Weight ratio of 10/1 (enzyme/oxidizing agent)

(6) Types of Oxidizing Agents

Oxidizing agent powders (b2) with a small particle diameter were obtained from passing fractions, through JIS standard 500 μm sieve, of sodium perborate.4H$_2$O (product number 28-3630-5, manufactured by Wako Pure Chemical Industries, Ltd.) and sodium perchlorate.1H$_2$O (product number 193-08065, manufactured by Wako Pure Chemical Industries, Ltd.) respectively. The amount of effective oxygen in 1 g of each kind of oxidizing agent was 0.12 g in the case of sodium perborate.4H$_2$O or 0.03 g in the case of sodium perchlorate.1H$_2$O. 3.0 g of Duramyl 60T (a1) prepared in (1) above and 0.3 g of the oxidizing agent powder (b2) were mixed in a weight ratio (enzyme/oxidizing agent) of 10/1 in glass bottles (No. 3, manufactured by Maruemu Corporation), then capped, and contacted with each other at 25° C. and absolute humidity: 8 g/m$^3$ for 30 minutes. These mixtures were separated by JIS standard 500 μm sieve. When the enzyme activity of the separated Duramyl 60T was measured by the method described above, the present products had a higher enzyme activity than that of the enzyme (control) not contacted with the oxidizing agent (Table 3).

TABLE 3

| Oxidizing agent | Relative activity (%) |
|---|---|
| Sodium perborate•4H$_2$O | 140 |
| Sodium perchlorate•1H$_2$O | 120 |

*Contact ratio:Weight ratio of 10/1 (enzyme/oxidizing agent)

(7) Particle Diameter of the Oxidizing Agent 3.0 g of a passing fraction, through JIS standard 500 μm sieve, of Duramyl 60T (a1) [(a2), average particle diameter (median diameter): 380 μm] and 0.3 g of a fraction of non-milled SPC-D remaining on JIS standard 500 μm sieve [(b3), average particle diameter (median diameter) 879 μm, indicated as "Not milled" in Table 4] were mixed in a weight ratio (enzyme/oxidizing agent) of 10/1 in glass bottles (No. 3, manufactured by Maruemu Corporation), then capped, and contacted with each other at 25° C. at 8 g/m$^3$ for 30 minutes. These mixtures were separated by JIS standard 500 μm sieve. Separately, Duramyl 60T (a1) and the oxidizing agent powder with a small particle diameter [indicated as "Milled" in the table] obtained from a fraction passing through JIS standard 500 μm sieve were treated in the same manner as described above. When the enzyme activity of the separated Duramyl 60T was measured by the method described above, the present products regardless of the particle diameter of the oxidizing agent had a higher enzyme activity than that of the enzyme (control) not contacted with the oxidizing agent (Table 4).

TABLE 4

| Used enzyme | Form of oxidizing agent | Relative activity (%) |
|---|---|---|
| (a1) | Milled | 150 |
| (a2) | Not milled | 148 |

*Contact ratio:weight ratio of 10/1 (enzyme/oxidizing agent)

(8) Activation of α-Amylase by Using the Recovered Oxidizing Agent

When the oxidizing agent after contacting, used in (2) in Example 1, was recovered and then contacted by the method in (2) above with Duramyl 60T (a1) [prepared in (1) above] not contacted with the oxidizing agent, the product of the present invention had a higher enzyme activity than the enzyme (control) not contacted with the oxidizing agent.

(9) Enzyme After Separation

The enzyme separated from the oxidizing agent powder (b1) in (3) in Example 1 was placed in glass bottles (No. 3, manufactured by Maruemu Corporation), then capped, and stored at 25° C. and absolute humidity: 8 g/m$^3$ for 30 days. When the enzyme activity of Duramyl 60T was measured by the method described above, the enzyme had a high activity even after storage.

Example 2

When Termamyl 60T or Stainzyme 12T commercially available from Novozymes A/S was treated in the same manner as in (1), (3) and (5) in Example 1 and measured for α-amylase activity, the present products had a higher activity than that of the enzyme (control) not contacted with the oxidizing agent (Table 5). The enzyme activities of Termamyl 60T [(a3), average particle diameter (median diameter): 700

μm] and Stainzyme 12T [(a4), average particle diameter (median diameter): 652 μm] before the contacting step were 10000 IU/g and 180000 IU/g, respectively.

TABLE 5

| Contact temperature | Contact absolute humidity | Contact time | Relative activity (%) Termamyl 60T (a3) | Relative activity (%) Stainzyme 12T (a4) |
|---|---|---|---|---|
| 25° C. | 8 g/m³ | 5 minutes | 110 | 110 |
|  | 8 g/m³ | 30 minutes | 120 | 120 |
| 40° C. | 43 g/m³ | 30 minutes | 120 | 137 |

*Contact ratio:weight ratio of 10/1 (enzyme/oxidizing agent)

Example 3

When Purastar OxAm commercially available from Genencor International Inc. was treated in the same manner as in (1), (3), (4) and (5) in Example 1 and measured for α-amylase activity, the present products had a higher activity than that of the enzyme (control) not contacted with the oxidizing agent (Table 5). The enzyme activity of Purastar OxAm (Purastar OxAm) [(a5), average particle diameter (median diameter): 679 μm] before the contacting step was 37000 IU/g.

TABLE 6

| Contact temperature | Contact absolute humidity | Contact time | Relative activity (%) |
|---|---|---|---|
| 25° C. | 8 g/m³ | 5 minutes | 120 |
|  |  | 30 minutes | 120 |
|  |  | 3 days | 135 |
| 50° C. | 8 g/m³ | 30 minutes | 121 |
| 40° C. | 43 g/m³ | 30 minutes | 145 |

*Contact ratio:weight ratio of 10/1 (enzyme/oxidizing agent)

Example 4

0.5 wt % Duramyl 60T (a1) contacted with the oxidizing agent (weight ratio of 10/1 (enzyme/oxidizing agent)) in Example 1, and 0.5 wt % perfume, were incorporated into 99 wt % detergent base described in Example 3 in WO99/29830, to give a detergent composition A. Separately, a detergent composition B was obtained by incorporation of 0.5 wt % Duramyl 60T (a1) not treated with the oxidizing agent, in place of the above Duramyl 60T (a1).

The detergent composition A or B was dissolved at a concentration for use (concentration of 1 wt %) in 1 L tap water regulated at 30° C., and then transferred to a stainless beaker for Terg-O-Tometer (manufactured by Ueshima Seisakusho Co., Ltd.). Starch/dye-stained five clothes (EMPA162) (6 cm×6 cm) were placed in the resulting detergent solution, stirred and washed at 80 rpm for 10 minutes. After washing with running water, the clothes were pressed and measured for their reflectance. The reflectance of a raw cloth used to prepare the stained cloth, and the reflectance of the artificially stained cloth before and after washing, were measured at 460 nm with an automatic color difference meter (Shimadzu Corporation) to determine the degree of washing (%). As a result, it was confirmed that the detergent composition A had higher detergency than that of the detergent composition B.

Example 5

(1) Preparation of Stained Dishes

China plates of 25 cm in diameter were boiled in boiling tap water, and soft cooked rice was left for 30 minutes at room temperature (25° C.), and then 3 g of the rice was spread over each of the China plates, dried at room temperature for about 3 hours, and stored (in a semi-sealed state) at 5° C. just before use.

(2) Washing Conditions

The contaminated dishes were washed under the following conditions. Three stained dishes were washed each time.

Used machine: Automatic dish washer NP-810 manufactured by Matsushita Electronic Industry Co., Ltd.

Washing temperature: Gradual increase in temperature from water temperature to about 55° C.

Washing water: tap water (ca. 4° DH)

Detergent concentration: 0.2 wt %.

Washing time: washing for about 20 minutes→rinsing for about 20 minutes (standard course)

Amount of circulating water during washing: 3.5 L.

Used detergent compositions: shown in Table 7.

TABLE 7

| Component | Detergent composition C | Detergent composition D |
|---|---|---|
| Pluronic L-61[1] | — | — |
| Softanol EP-7085[2] | 4.0 | 4.0 |
| Trisodium citrate | — | — |
| Sodium tripolyphosphate | 30.0 | 30.0 |
| Sodium percarbonate | 20.0 | 20.0 |
| Sodium carbonate | 10.0 | 10.0 |
| Amorphorous silicate[3] | 4.0 | 4.0 |
| AA-MA[4] | 10.0 | 10.0 |
| Sodium sulfate | 1.0 | 1.0 |
| Activated α-amylase[5] | 1.0 |  |
| Untreated α-amylase[6] | — | 1.0 |

[1]Polyoxyethylene/polyoxypropylene copolymer (weight-average molecular weight 2,000, manufactored by Asahi Denka Kogyo K.K.)
[2]A C12 to C14 sec-alcohol adduct ahving 7 moles on average of ethyylene oxide and 8.5 moles on average of propylene oxide added thereto (random adduct)
[3]Sodium silicate JIS No. 2
[4]An acrylic acid/ maleic acid copolymer (acrylic acid/maleic acid = 70/30 molar ratio, weight-average molecular weight 6000)
[5]Duramyl 60T (a1) used in Example 4 [after treatment in a weight ratio of 10/1 (enzyme/oxidizing agent) in Example 1]
[6]Duramyl 60T (a1) (control) not treated with the oxidizing agent After the wash, each soiled plate was dyed with 5 ml of 5 mmol/L iodine solution, which had been obtained by diluting 0.05 mol/L iodine solution (product number 15-0620-5, manufactured by SIGMA-ALDRICH, Inc.) by 10% with ion-exchange water. Their washing performances were compared by visual judgment. As a result, the detergent composition C containing activated α-amylase had extremely higher detergency than that of the detergent composition D containing untreated α-amylase.

Example 6

0.5 wt % activation-treated mixture of Duramyl 60T (a1) and oxidizing agent powder (b1) [weight ratio of 10/1 (enzyme/oxidizing agent), not separated from each other] prepared in the item of mixing ratio in (2) in Example 1 and 0.5 wt % perfume were incorporated into 99 wt % detergent base described in Example 3 in WO99/29830, to give a detergent composition E. As control, a detergent composition F was obtained by incorporation of 0.455 wt % Duramyl 60T (a1) not treated with the oxidizing agent, 0.045 wt % oxidizing agent powder (b1), and 0.5 wt % perfume into 99 wt % of the same detergent base.

As a result of the comparison of detergency between the two detergent compositions by the detergency method described in Example 4, it was confirmed that the detergent composition E had higher detergency than that of the detergent composition F.

The invention claimed is:

1. A method of activating α-amylase, which comprises steps of contacting A) α-amylase or particles comprising α-amylase with B) particles comprising an oxidizing agent and separating, after the contacting step, A) the α-amylase or particles comprising α-amylase from B) particles comprising the oxidizing agent, wherein the particles comprising an oxidizing agent have a diameter of 100 μm to 1500 μm, wherein the ratio of enzyme to oxidizing agent is from 1:10 to 100:1, and wherein the activity of said α-amylase is increased by 20 to 101% as compared to α-amylase which is not contacted with an oxidizing agent, and wherein the activity of the α-amylase particles is maintained after the separation step.

2. A method of producing particles comprising activated α-amylase, which comprises steps of contacting A) particles comprising α-amylase with B) particles comprising an oxidizing agent and separating, after the contacting step, A) the particles comprising α-amylase from B) particles comprising the oxidizing agent, wherein the particles comprising an oxidizing agent have a diameter of 100 μm to 1500 μm, wherein the ratio of enzyme to oxidizing agent is from 1:10 to 100:1, wherein the activity of said α-amylase is increased by 20 to 101% as compared to α-amylase which is not contacted with an oxidizing agent, and wherein the activity of the α-amylase particles is maintained after the separation step.

3. The method according to claim 1, wherein the activation step is carried out in the absence of any other particles than A) and B).

4. The method according to claim 2, wherein the activation step is carried out in the absence of any other particles than A) and B).

5. The method according to claim 1, wherein the activating step is carried out by mixing particles consisting essentially of A) particles and B) particles.

6. The method according to claim 2, wherein the activating step is carried out by mixing particles consisting essentially of A) particles and B) particles.

7. The method according to claim 1, wherein A) particles are different from B) particles in particle size.

8. The method according to claim 2, wherein A) particles are different from B) particles in particle size.

9. The method according to claim 1, wherein the contacting is conducted from 30 seconds to 50 days.

10. The method according to claim 2, wherein the contacting is conducted from 30 seconds to 50 days.

11. The method according to claim 1, wherein the contacting is conducted from 10 seconds to 2 months, wherein the contacting temperature is from 20° C. to 50° C., and wherein the contacting humidity is 0.5 g/m$^3$ to 1000 g/m$^3$ in the ambient.

12. The method according to claim 2, wherein the contacting is conducted from 10 seconds to 2 months, wherein the contacting temperature is from 20° C. to 50° C., and wherein the contacting humidity is 0.5 g/m$^3$ to 1000 g/m$^3$ in the ambient.

13. The method according to claim 1, wherein the separating step comprises a screening step and/or an air classification step.

14. The method according to claim 2, wherein the separating step comprises a screening step and/or an air classification step.

15. The method according to claim 1, wherein the oxidizing agent comprises percarbonate, perborate, persulfate, permanganate or perchlorate.

16. The method according to claim 2, wherein the oxidizing agent comprises percarbonate, perborate, persulfate, permanganate or perchlorate.

17. The method according to claim 1, wherein the activity of said α-amylase is increased by 20 to 70%.

18. The method according to claim 2, wherein the activity of said α-amylase is increased by 20 to 70%.

19. The method according to claim 1, wherein the activity of said α-amylase is increased by 20 to 40%.

20. The method according to claim 2, wherein the activity of said α-amylase is increased by 20 to 40%.

* * * * *